US008866475B2

(12) United States Patent
Chen et al.

(10) Patent No.: US 8,866,475 B2
(45) Date of Patent: Oct. 21, 2014

(54) METHOD FOR CORRECTING NMR AND NUCLEAR LOGS IN FORMATE MUD FILTRATE INVADED FORMATIONS

(75) Inventors: Songhua Chen, Katy, TX (US); W. Allen Gilchrist, Jr., Fort Davis, TX (US)

(73) Assignee: Baker Hughes Incorporated, Houston, TX (US)

( * ) Notice: Subject to any disclaimer, the term of this patent is extended or adjusted under 35 U.S.C. 154(b) by 378 days.

(21) Appl. No.: 13/289,094

(22) Filed: Nov. 4, 2011

(65) Prior Publication Data

US 2013/0113479 A1    May 9, 2013

(51) Int. Cl.
*G01V 3/32* (2006.01)
*E21B 49/08* (2006.01)
*G01N 24/08* (2006.01)

(52) U.S. Cl.
CPC . *G01V 3/32* (2013.01); *E21B 49/08* (2013.01); *G01N 24/081* (2013.01)
USPC ......................................................... 324/303

(58) Field of Classification Search
CPC ....................................................... G01V 3/32
USPC ................................................. 324/300–322
See application file for complete search history.

(56) References Cited

U.S. PATENT DOCUMENTS

| 4,158,165 | A | | 6/1979 | Coates |
| 4,769,606 | A | | 9/1988 | Vinegar et al. |
| 5,585,720 | A | * | 12/1996 | Edwards ........................ 324/309 |
| 5,764,058 | A | * | 6/1998 | Itskovich et al. ............. 324/303 |
| 6,163,153 | A | * | 12/2000 | Reiderman et al. ........... 324/314 |
| 6,331,775 | B1 | * | 12/2001 | Thern et al. .................... 324/303 |
| 6,429,654 | B1 | * | 8/2002 | Itskovich et al. ............. 324/314 |
| 6,690,167 | B2 | * | 2/2004 | Reiderman et al. ........... 324/314 |
| 2002/0059028 | A1 | | 5/2002 | Rozak |
| 2004/0032257 | A1 | | 2/2004 | Freedman |
| 2009/0248309 | A1 | | 10/2009 | Neville et al. |

OTHER PUBLICATIONS

Freedman, et al. "Field Applications of a New Nuclear Magnetic resonance Fluid Characterization Method". SPE 71713. SPE Annual technical Conference and Exhibition held in new Orleans, Louisiana, Sep. 30-Oct. 3, 2001. pp. 1-12.
International Search Report and Written Opinion for corresponding PCT Application No. PCT/US2012/058512, dated Mar. 15, 2013, pp. 1-10.

* cited by examiner

*Primary Examiner* — Dixomara Vargas
(74) *Attorney, Agent, or Firm* — Cantor Colburn LLP

(57) ABSTRACT

A method of calculating a porosity of a geological formation includes determining a bulk pore volume and a movable fluid pore volume in the geological formation in which drilling mud including a mud filtrate is introduced, calculating a porosity of the formation based on a bulk pore volume, and correcting the porosity based on the movable fluid volume in the geological formation.

19 Claims, 6 Drawing Sheets

US 8,866,475 B2

METHOD FOR CORRECTING NMR AND NUCLEAR LOGS IN FORMATE MUD FILTRATE INVADED FORMATIONS

BACKGROUND

Drilling mud, or drilling fluid, is provided during a drilling operation to provide various benefits including keeping a drill clean, removing cuttings from a bore hole, providing hydrostatic pressure to prevent fluids in a rock formation from entering the bore hole, and other benefits. The drilling mud comprises a fluid or filtrate, such as water and chemicals, and particulates, such as clay.

In a drilling operation, information regarding the formation is obtained by a wire line (WL) or by logging while drilling (LWD). The wire line data is obtained after the bore hole has been drilled, and the wire line equipment is inserted into the bore hole to obtain data. On the other hand, the LWD data is obtained simultaneously with the drilling operation.

Methods of logging include nuclear magnetic resonance (NMR) logging, neutron logging, and density logging. In NMR logging, a portion of a geological or rock formation is placed within magnetic fields to alter the magnetic state of the molecules in the formation. The characteristics of the formation are detected, including a $T_2$ spectrum, which corresponds to the times for the molecules to return from an altered magnetic state to a relaxation state. The $T_2$ spectrum is used to determine characteristics of the formation, such as porosity, or pore volume, and relative volumes of bound fluids and movable fluids in the geological formation.

In a LWD operation, various factors change measured characteristics of the formation including invasion of the filtrate into the formation and a slow-forming mud cake in the bore hole. These factors introduce uncertainties and variables in the calculations of density and hydrogen indexes in LWD operations.

SUMMARY

Disclosed is a method of calculating a porosity of a formation, the method comprising drilling a bore hole in the formation with a drill and drilling mud including a mud filtrate; determining a bulk pore volume and a movable fluid pore volume in the formation; calculating a porosity of the formation based on the bulk pore volume; and correcting the porosity based on the movable fluid pore volume.

Also disclosed is a method of calculating a porosity of a geological formation having a bore hole drilled by a drill including a drilling mud having a mud filtrate, the method comprising determining a bulk pore volume of the formation; determining a portion of the bulk pore volume that corresponds to a movable fluid pore volume of the formation; and calculating a porosity of the formation by adjusting a hydrogen index value of the movable fluid pore volume to correspond to a hydrogen index of the mud filtrate, and by leaving a hydrogen index of the rest of the bulk pore volume unadjusted, or adjusting a hydrogen index to a value different from the hydrogen index of the mud filtrate.

BRIEF DESCRIPTION OF THE DRAWINGS

Referring now to the drawings wherein like elements are numbered alike in the several Figures.

DETAILED DESCRIPTION

Figure 1:
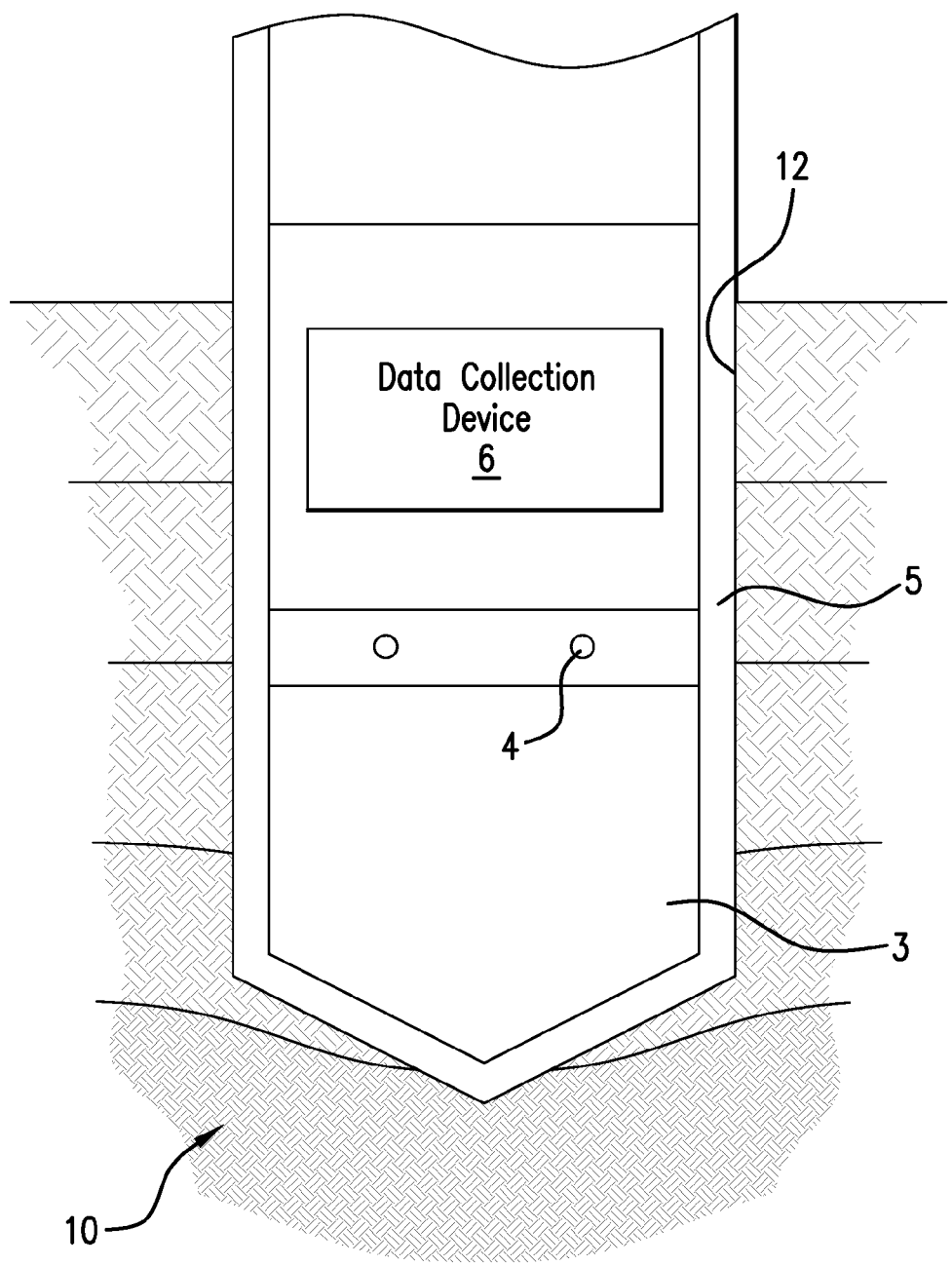
FIG. 1 depicts a drill bit and drilling fluid in a bore hole.

FIG. 1 illustrates an example of a drill pipe 2 having at its end a drill bit 3. The drill bit 3 rotates to break up the geological or rock formation 10 to lengthen the bore hole 12. Drilling mud 5 is pumped into the bore hole 12 via openings 4 located at or near the drill bit 3 and the drilling mud 5 fills the bore hole 12. In the present embodiment, the filtrate of the drilling mud 5 includes formate.

During drilling, particulates in the drilling mud 5 form a mud cake, or filter cake, between the bore hole 12 and the formation 10. Some mud filtrate of the drilling mud 5 passes through the mud cake to mix with movable fluids in the formation 10.

A log data collection device 6 is connected to the drill pipe 2 or drill bit 3, as illustrated in FIG. 1, and is inserted into the bore hole 12 simultaneously with the drill pipe 2. According to alternative embodiments, the data collection device 6 is inserted into the bore hole 12 after removal of the drill pipe 2 and drill bit 3. The data collection device 6 of FIG. 1 is a nuclear magnetic resonance (NMR) logging device. However, according to alternative embodiments, the data collection device is a proton logging device, a density logging device, or any other desired type of logging device. The NMR device detects characteristics of invaded portions of the formation, or portions in which the mud filtrate has penetrated.

Figure 2A:
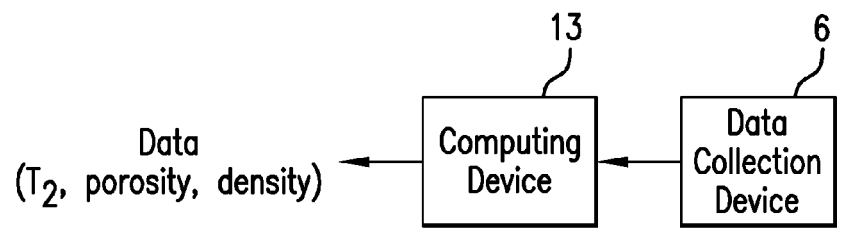
FIGS. 2A to 2C illustrate a log data collection device.
Figure 2B:
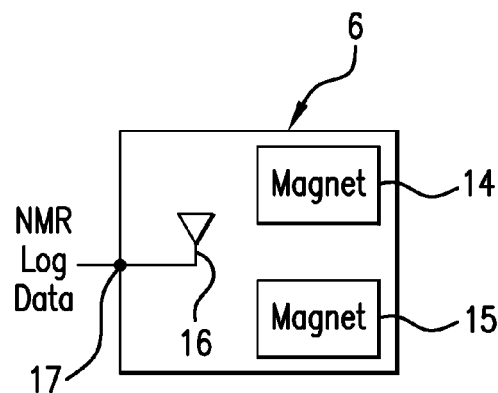
Figure 2C:
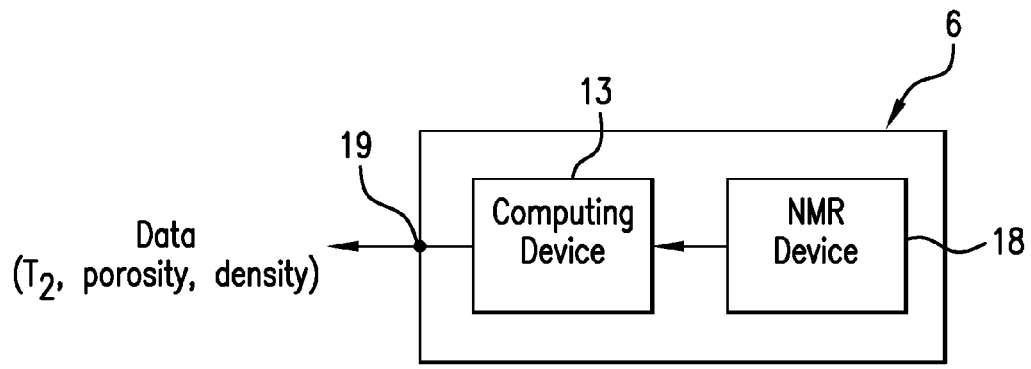

FIGS. 2A to 2C illustrate examples of structures of the data collection device 6. The data collection device includes elements, such as magnets, neutron generators, antenna, and sensors, to obtain data from the formation 10. The data is transmitted to a computing device 13, such as a processor or controller including the processor, memory, and supporting logic circuitry, to convert the data from the data collection device 6 into data to analyze the formation. The processed data includes $T_2$ values, porosity values, density, movable fluid/bound fluid ratios or volumes, permeability, or any other processed data. The processed data is then used to further control the drilling operation.

FIG. 2B illustrates an exemplary data collection device 6 that is an NMR device. The NMR device includes magnets 14 and 15 to generate magnetic fields, and an antenna 16 to detect electro-magnetic field intensities from the formation. According to one embodiment, the antenna 16 both creates an alternating electro-magnetic field pulse and detects electromagnetic field intensities. According to another embodiment, a separate antenna creates the alternating electro-magnetic field pulse. The NMR device transmits the collected data via a terminal 17 to a computing device 13 for processing. It is understood, as illustrated in FIG. 2C, that the NMR device 18 and computing device 13 may both be incorporated within a same data collection device. For example, the solid borders illustrated in FIG. 2C corresponds to an outer shell of a device, and the device includes one or more terminals 19 to output the processed data to one or more additional devices.

The computing device 13 receives the detected electromagnetic field intensity of the formation 10, and then calculates a $T_2$ spectrum based on the detected electro-magnetic field intensity. The computing device 13 generates a preliminary or bulk porosity value based on the $T_2$ spectrum. The computing device 13 corrects the preliminary porosity calculation by substituting a predetermined hydrogen index (HI) value corresponding to the mud filtrate for a portion of the detected bulk pore volume that corresponds to movable fluids. The computing device 13 then outputs the corrected porosity value based on the corrected HI.

The computing device 13 includes computing circuitry such as semiconductor chips, integrated circuits, and printed circuit board assemblies.

Figure 3:
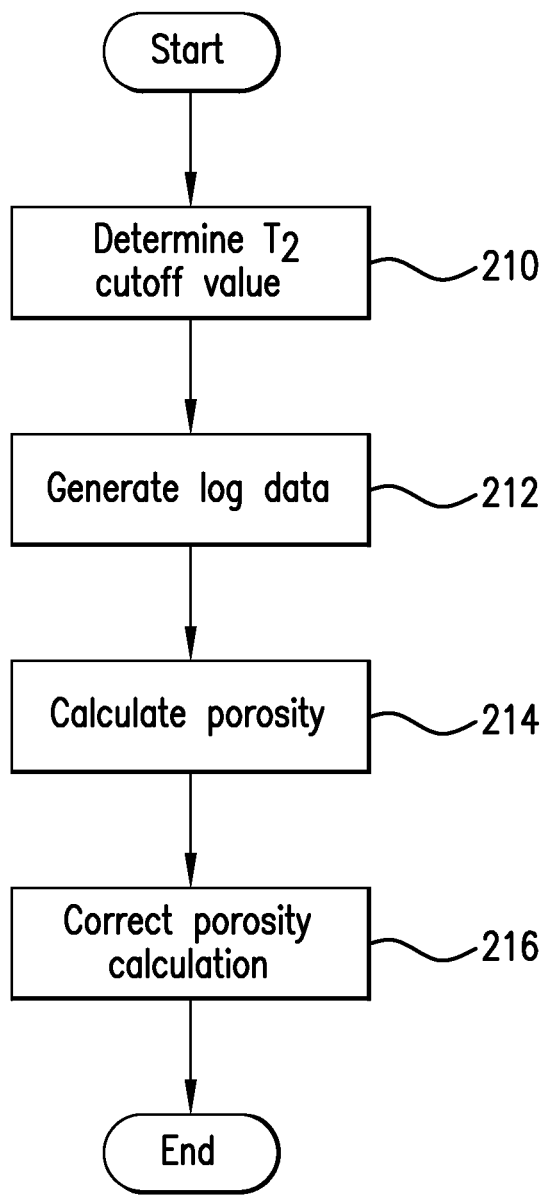
FIG. 3 illustrates a method of calculating a porosity of a formation in a logging-while-drilling operation.

FIG. 3 illustrates a method of correcting a porosity calculation. In operation 210 a $T_2$ cutoff value is determined. The $T_2$ cutoff value indicates a $T_2$ boundary between bound fluid and movable fluid. In particular, a $T_2$ measurement measures a transverse relaxation in the formation, or the loss of coherent energy by protons in the formation. This occurs as an electro-magnetic field amplitude of the formation decreases after having been increased by magnetic pulses from an NMR device. Since movable fluid has a different $T_2$ response than bound fluid, a $T_2$ cutoff may be calculated which correspond to the boundary of $T_2$ values of the movable fluid and the bound fluid, respectively.

Once the $T_2$ cutoff value is determined, log data is generated in operation 212. The log data is generated by an NMR device, a neutron log device, a density log device, an EP log device, or any other log device. Each respective log device is used to determine a porosity of the formation 10 in operation 214.

Once the porosity of the formation is determined, the porosity is corrected in operation 216 using the $T_2$ spectrum and the $T_2$ cutoff, which is used to determine the pore volume of the formation that corresponds to movable fluid.

When drilling with a drilling mud, the mud filtrate invades only the pores of the formation 10 which correspond to movable fluid. The bound fluid volume is not invaded by the filtrate. Therefore, a calculation of the porosity takes into account only the invasion of the filtrate into the pore volume corresponding to movable fluid in the formation. Since the bound fluid volume is not invaded by the filtrate, the porosity of the pore volume corresponding to the bound fluid remains un-corrected. The resulting porosity calculation more accurately corresponds to the actual porosity, since the porosity calculation is not over-corrected by correcting the pore volume corresponding to the bound fluid.

Figure 4:
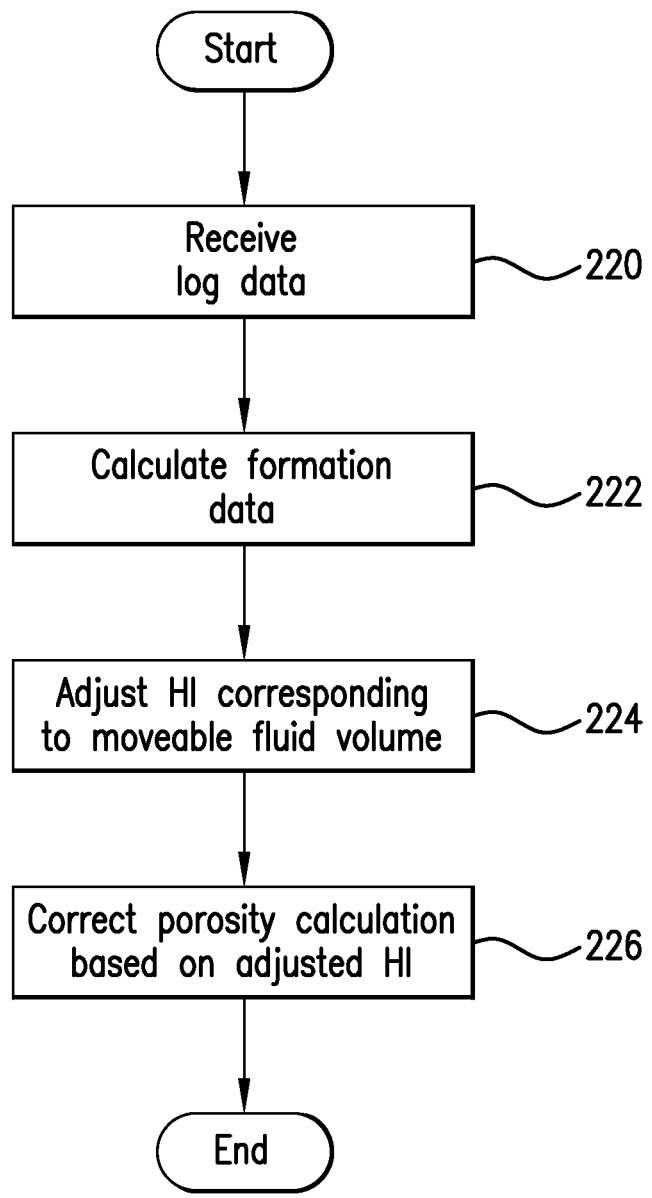
FIG. 4 illustrates an operation of correcting a calculated porosity.

The operations of calculating porosity 214 and correcting the porosity calculation 216 are described in further detail in FIG. 4.

In operation 220 log data is received. For example, an NMR device, neutron log device, or density log device detects field intensity levels corresponding to the respective devices.

Based on the received log data, characteristics of the formation are calculated in operation 222. For example, a bulk pore volume, movable fluid pore volume, and bound fluid pore volume are calculated.

The hydrogen index (HI) is one factor that contributes to the detected signal levels of the log devices. However, the invasion of filtrate into the formation alters the hydrogen index within the formation, and the HI value should be adjusted accordingly in operation 224. In particular, since adjusting the HI of the total pore volume would result in an over-correction and inaccurate calculated porosity, the HI of the pore volume corresponding only to the movable fluids is adjusted, and the HI of the pore volume corresponding to the bound fluids is unchanged, or adjusted to a hydrogen index value different from the hydrogen index of the mud filtrate. Consequently, in operation 226, the porosity calculation is corrected to incorporate the adjusted HI of the portion of the pore volume corresponding to the movable fluid and the non-adjusted HI of the portion of the pore volume corresponding to the bound fluids.

The resulting porosity calculation is a value closer to the actual porosity than either a porosity calculated without any HI adjustment or a porosity calculated having an HI adjustment of the bulk pore volume, including the movable and bound fluid volumes.

Figure 5:
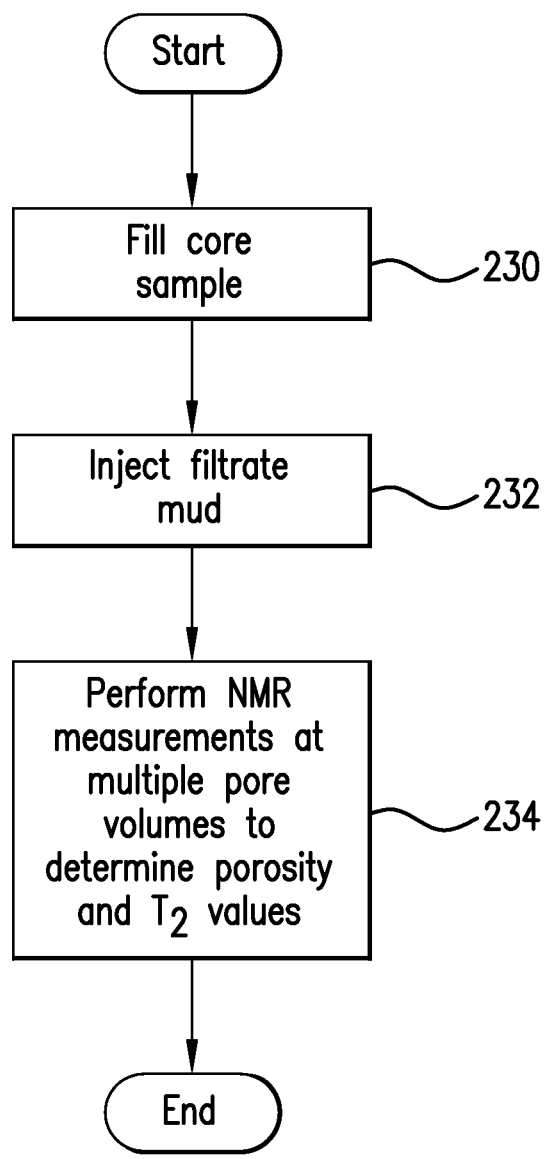
FIG. 5 illustrates a method of verifying a $T_2$ cutoff value according to one disclosed embodiment.
Figure 6:
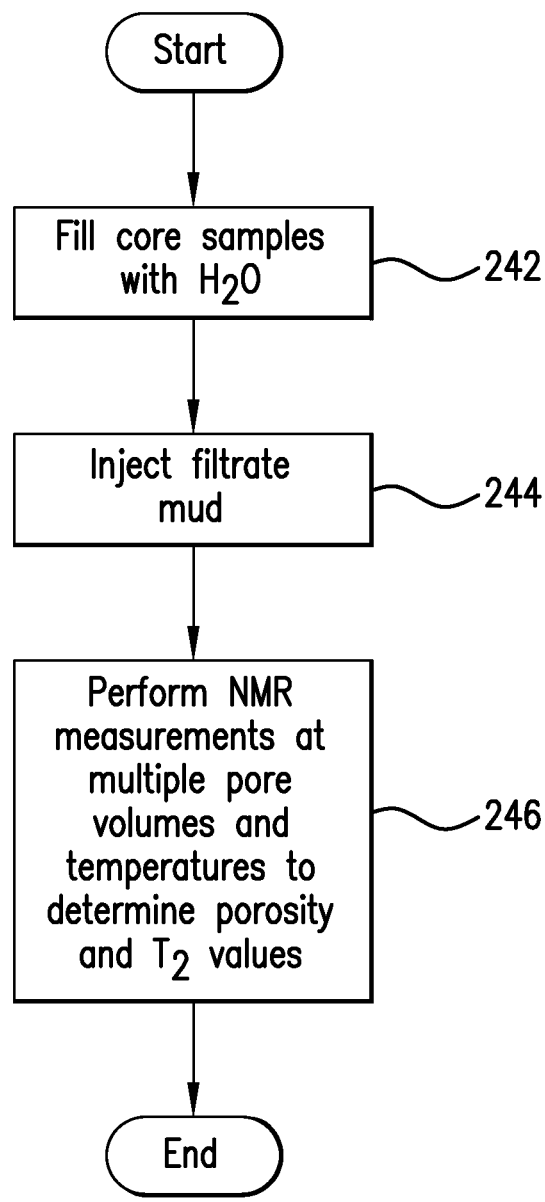
FIG. 6 illustrates a method of verifying the $T_2$ cutoff value according to another disclosed embodiment.

Since the $T_2$ cutoff value is affected by fluid-rock matrix interactions, calibration is required to obtain a correct $T_2$ cutoff value before the correction operation is performed. FIGS. 5 and 6 illustrate operations to calibrate a correct $T_2$ cutoff value or verify a corrected porosity value.

Referring to FIG. 5, in operation 230, core samples from the drilled formation are filled with a fluid. In a first phase of the operation, fluid not containing hydrogen or not responsive to NMR excitation is injected into a core sample. For example, the fluid has a chemical formula of, e.g., $D_2O$, where D is deuterium, an isotope of hydrogen that does not respond to NMR excitation targeted on Hydrogen nuclei. In operation 232, the core sample is then injected with filtrate solution. In operation 234, NMR measurements are taken as the core sample is injected with the filtrate. The NMR measurements are taken at multiple pore volumes, and porosity and $T_2$ distributions are calculated.

In a second phase of the operation, the core samples are filled with a filtrate solution in operation 230, and operations 232 and 234 are repeated. The resulting measurements are compared with the measurements of the first phase, in which the core samples were filled with, e.g., $D_2O$, for comparison. The comparison of the first and second phase measurements will identify the movable fluid part of the $T_2$ spectrum and hence allow selection of the $T_2$ cutoff.

Referring to FIG. 6, in operation 242, core samples from the formation are filled with $H_2O$. In operation 244, the samples are injected with a filtrate solution, and in operation 246, NMR measurements are taken at multiple pore volumes and two slightly different temperatures to determine porosity and $T_2$ distributions. Specifically, at each volume, NMR measurements are taken at a temperature slightly above the freezing temperature of water, such as within ten degrees of the freezing temperature of water. NMR measurements are then taken at a temperature slightly below the freezing temperature of water, but above the freezing temperature of the filtrate solution. Comparing the $T_2$ values at each temperature based on the NMR measurements provides the $T_2$ distribution of the movable fluid and hence selection of the $T_2$ cutoff.

While one or more embodiments have been shown and described, modifications and substitutions may be made thereto without departing from the spirit and scope of the invention. Accordingly, it is to be understood that the present invention has been described by way of illustrations and not limitation.

The invention claimed is:

1. A method of calculating a porosity of a geological formation, the method comprising:
   determining, by a processor of a computing device, a bulk pore volume and a movable fluid pore volume in the geological formation in which drilling mud including a mud filtrate is introduced based on measurements by a data collection device in a borehole of the geological formation;
   calculating, by the processor of the computing device, a porosity of the geological formation based on the bulk pore volume; and
   correcting, by the processor of the computing device, the calculated porosity based on the movable fluid pore volume to take into account a difference in characteristics between the movable fluid pore volume and a bound fluid pore volume.

2. The method of claim 1, wherein correcting the calculated porosity includes adjusting the calculated porosity based on characteristics of the mud filtrate in the movable fluid pore volume.

3. The method of claims 2, wherein correcting the calculated porosity includes adjusting a hydrogen index of the geological formation to compensate for a presence of the mud filtrate in the movable fluid pore volume.

4. The method of claim 3, wherein correcting the calculated porosity includes not adjusting a hydrogen index value corresponding to a bound fluid pore volume to account for an absence of the mud filtrate in bound fluid pore volume portions of the geological formation.

5. The method of claim 1, wherein the porosity is calculated using nuclear magnetic resonance, and
determining the movable fluid pore volume includes using a $T_2$ cutoff value separating movable and bound fluids in the geological formation.

6. The method of claim 5, further comprising, prior to calculating the porosity of the geological formation, determining the $T_2$ cutoff value separating movable and bound fluids in the geological formation.

7. The method of claim 6, wherein determining the $T_2$ cutoff value comprises:
filling core samples from the geological formation with a molecule $D_2O$, where D is deuterium;
injecting the core samples with the mud filtrate;
taking NMR measurements of the core samples at a plurality of distributions of bound fluid and movable fluid pore volumes; and
repeating the NMR measurements after removing the $D_2O$ and filling the core samples with only the mud filtrate.

8. The method of claim 6, wherein determining the $T_2$ cutoff value comprises:
filling core samples with $H_2O$;
injecting the core samples with the mud filtrate;
taking NMR measurements of the core samples at a plurality of distributions of bound fluid and movable fluid pore volumes, and taking the NMR measurements at two different temperatures for each volume; and
repeating the NMR measurements after removing the $H_2O$ and filling the core samples with only the mud filtrate.

9. The method of claim 8, wherein the two different temperatures are a temperature above a freezing temperature of water and a temperature below the freezing temperature of water but above a freezing temperature of the mud filtrate.

10. The method of claim 1, wherein the porosity is calculated using a neutron porosity log.

11. The method of claim 10, wherein correcting the porosity includes adjusting a hydrogen index value corresponding to movable fluid of the movable fluid pore volume to compensate for a presence of the mud filtrate in the movable fluid pore volume, and not adjusting a hydrogen index value corresponding to bound fluid of a bound fluid pore volume to account for an absence of the mud filtrate in the bound fluid pore volume.

12. The method of claim 10, wherein the movable fluid pore volume in the geological formation is determined using nuclear magnetic resonance.

13. The method of claim 1, wherein calculating the porosity includes obtaining at least one of a density log and a photoelectric (PE) log.

14. The method of claim 13, wherein the movable fluid pore volume in the geological formation is determined using nuclear magnetic resonance.

15. The method of claim 13, wherein calculating the porosity includes obtaining the density log, and
the method further comprises determining whether the geological formation is a hydrocarbon-bearing formation, and applying the following equation when the geological formation is a non-hydrocarbon-bearing formation:

$$\rho_b = (1-\phi)\rho_m + \frac{BW \cdot \phi}{BW+BVM}\rho_w + \frac{BVM \cdot \phi}{BW+BVM}\rho_{Formate},$$

where $\rho_b$ is a bulk density of the geological formation, $\phi$ is the calculated porosity, $\rho_m$ is a matrix density, BW is a bound fluid pore volume in the geological formation, BVM is the movable fluid pore volume in the geological formation, and $\rho_{Formate}$ is a density of the mud filtrate.

16. The method of claim 13, further comprising determining whether the geological formation is a hydrocarbon-bearing formation, and applying the following equation when the geological formation is a hydrocarbon-bearing formation:

$$\rho_b = \\ (1-\phi)\rho_m + \frac{BW \cdot \phi}{BW+BVM}\rho_w + \frac{V_{xo} \cdot \phi}{BW+BVM}\rho_o + \frac{(BVM-V_{xo}) \cdot \phi}{BW+BVM}\rho_{Formate},$$

where $\rho_b$ is a bulk density of the geological formation, $\phi$ is the calculated porosity, $\rho_m$ is a matrix density, BW is a bound fluid pore volume in the geological formation, BVM is the movable fluid pore volume in the geological formation, $\rho_{Formate}$ is a density of the mud filtrate, $\rho_o$ is a density of a hydrocarbon in the hydrocarbon-bearing formation, and $V_{xo}$ is a volume of the hydrocarbon.

17. A method of calculating a porosity of a geological formation having a bore hole drilled by a drill including a drilling mud having a mud filtrate, the method comprising:
determining, by a processor of a computing device, a bulk pore volume of the geological formation based on measurements by a data collection device in the borehole of the geological formation;
determining a portion of the bulk pore volume that corresponds to a movable fluid pore volume of the geological formation; and
calculating, by the processor of the computing device, a porosity of the geological formation by adjusting a hydrogen index value of the movable fluid pore volume to correspond to a hydrogen index of the mud filtrate, and by leaving a hydrogen index of the rest of the bulk pore volume un-adjusted to take into account a difference in characteristics between the movable fluid pore volume and a bound fluid pore volume.

18. The method of claim 17, wherein determining the bulk pore volume and the movable fluid pore volume includes performing nuclear magnetic resonance (NMR) operation on the geological formation.

19. The method of claim 18, further comprising using a $T_2$ cutoff value on an NMR log generated by performing the NMR operation.

* * * * *